United States Patent
Grill et al.

(10) Patent No.: US 7,623,925 B2
(45) Date of Patent: *Nov. 24, 2009

(54) METHODS FOR SELECTIVELY STIMULATING COMPONENTS IN, ON, OR NEAR THE PUDENDAL NERVE OR ITS BRANCHES TO ACHIEVE SELECTIVE PHYSIOLOGIC RESPONSES

(75) Inventors: Warren M Grill, Cleveland, OH (US); Kenneth J Gustafson, Shaker Heights, OH (US); Graham H Creasey, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 895 days.

This patent is subject to a terminal disclaimer.

(21) Appl. No.: 11/141,457

(22) Filed: May 31, 2005

(65) Prior Publication Data
US 2005/0222636 A1    Oct. 6, 2005

Related U.S. Application Data

(62) Division of application No. 10/113,828, filed on Mar. 29, 2002, now Pat. No. 6,907,293.

(60) Provisional application No. 60/280,222, filed on Mar. 30, 2001.

(51) Int. Cl.
    *A61N 1/36* (2006.01)
(52) U.S. Cl. .............................. 607/41; 607/39; 607/40
(58) Field of Classification Search ............. 607/39–41, 607/2, 62, 118, 138
    See application file for complete search history.

(56) References Cited

U.S. PATENT DOCUMENTS

| | | | |
|---|---|---|---|
| 3,727,616 A | 4/1973 | Lenzkes |
| 3,870,051 A | 3/1975 | Brindley |
| 3,941,136 A | 3/1976 | Bucalo |
| 4,406,288 A | 9/1983 | Horwinski et al. |
| 4,585,005 A | 4/1986 | Lue et al. |
| 4,607,639 A | 8/1986 | Tanagho et al. |
| 4,703,755 A | 11/1987 | Tanagho et al. |
| 4,739,764 A | 4/1988 | Lue et al. |
| 4,771,779 A | 9/1988 | Tanagho et al. |
| 5,370,671 A | 12/1994 | Maurer et al. |
| 5,454,840 A | 10/1995 | Krakovsky et al. |
| 5,984,854 A | 11/1999 | Ishikawa et al. |
| 6,061,596 A | 5/2000 | Richmond et al. |

(Continued)

OTHER PUBLICATIONS

Grill, W.M., (2001) "Selective Activation of the Nervous System for Motor System Neural Prostheses", in Intelligent Systems and Technologies in Rehabilitation Engineering, H.-N. L. Teodorescu, L.C. Jain. Eds., CRC Press, 211-241.

(Continued)

*Primary Examiner*—Kennedy J Schaetzle

(57) ABSTRACT

Systems and methods selectively stimulate components of the pudendal nerve away from the sacral root to evoke desired physiologic responses in persons who lack the ability to otherwise produce these responses—e.g., maintain continence and/or produce micturition, and/or provide male/female sexuality responses, and/or provide bowel responses. The systems and methods use a multiple electrode array, or individual electrodes, placed on, in, or near the pudendal nerve. The electrode array, or individual electrodes, in association with a pulse generator, provide selective stimulation of individual fascicles within the pudendal nerve, to achieve different physiologic responses.

14 Claims, 4 Drawing Sheets

U.S. PATENT DOCUMENTS

| | | | |
|---|---|---|---|
| 6,266,557 | B1 | 7/2001 | Roe et al. |
| 6,366,814 | B1* | 4/2002 | Boveja et al. .................. 607/45 |
| 6,432,037 | B1 | 8/2002 | Eini et al. |
| 6,505,074 | B2 | 1/2003 | Boveja et al. |
| 6,650,943 | B1 | 11/2003 | Whitehurst et al. |
| 6,652,449 | B1 | 11/2003 | Gross et al. |
| 6,735,474 | B1 | 5/2004 | Loeb et al. |
| 6,836,684 | B1 | 12/2004 | Rijkhoff et al. |
| 6,907,293 | B2* | 6/2005 | Grill et al. .................... 607/39 |
| 6,941,171 | B2 | 9/2005 | Mann et al. |
| 2002/0055761 | A1 | 5/2002 | Mann et al. |
| 2002/0055779 | A1 | 5/2002 | Andrews |
| 2003/0004553 | A1 | 1/2003 | Grill et al. |
| 2003/0018365 | A1 | 1/2003 | Loeb |
| 2003/0100930 | A1 | 5/2003 | Cohen et al. |
| 2003/0114905 | A1 | 6/2003 | Kuzma |
| 2004/0030360 | A1 | 2/2004 | Elni et al. |
| 2004/0093093 | A1 | 5/2004 | Andrews |
| 2004/0111126 | A1 | 6/2004 | Tanagho et al. |
| 2004/0162594 | A1 | 8/2004 | King |

OTHER PUBLICATIONS

McNeal, D.R., B.R. Bowman (1985) Selective activation of muscles using peripheral nerve electrodes. Med. and Biol. Eng. and Comp. 23:249-253.

Starbuck, D.L., (1965) Myo-electric control of paralyzed muscles. IEEE Transactions on Biomedical Engineering. 12(3):169-172. Jul.-Oct.

Starbuck, D.L., Mortimer, J.T., Sheally C.N., Reswick, J.B. (1966) An implantable electrodes system for nerve stimulation. Proc. $19^{th}$ Ann. Conf. on Eng. in Med. and Biol. 8:38.

Caldwell, C (1971) Multielectrode Electrical Stimulation of Nerve in Development of Orthotic Systems Using Functional Electrical Stimulation and Myoelectric Control, Final Report Project # 19-P-58391-F-01, University of Lubljana, Faculty of Electrical Engineering, Lubljana, Yugoslavia.

McNeal, D.R. (1974) Selective Stimulation in Annual Reports of Progress Rehabilitation Engineering Center, Rancho Los Amigos Hospital, Downey, CA, pp. 24-25.

Wheeler et al, "Bladder Inhibition by Penile Nerve Stimulation in Spinal Cord Injury Patients", J Urol, Jan. 1992: 147(1):100-3.

Wheeler et al, "Management of Incontinent Sci Patients with Penile Stimulation: Preliminary Results", J Am Paraplegia Soc. Apr. 1994 17(2):55-9.

Sweeney, J.D., D.A. Ksienski, J.T. Mortimer (1990) A nerve cuff technique for selective excitation of peripheral nerve trunk regions. IEEE Trans. Biomed. Eng. 37:706-715.

Grill, W.M., J.T. Mortimer (1996) Quantification of recruitment properties of multiple contact cuff electrodes. IEEE Transactions on Rehabilitation Engineering 4(2):49-62.

Veraart, C., W.M. Grill, J.T. Mortimer (1993) Selective control of muscle activation with a multipolar nerve cuff electrode. IEEE Trans. Biomed. Engineering 40:640-653.

* cited by examiner

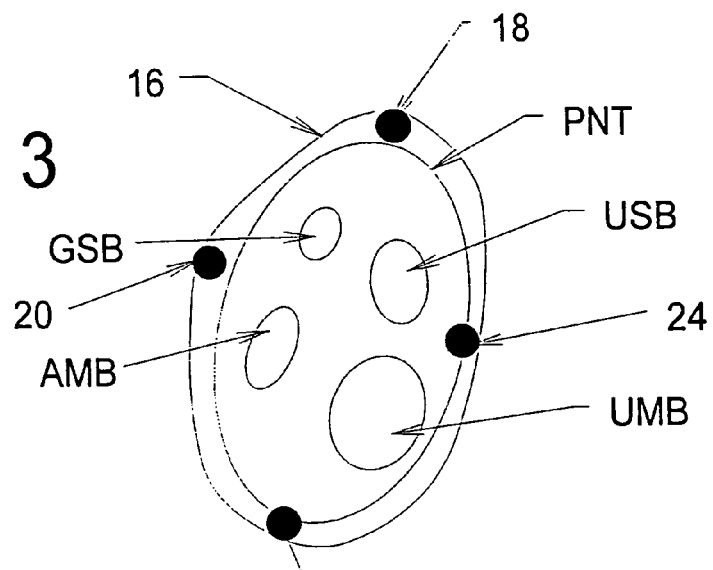
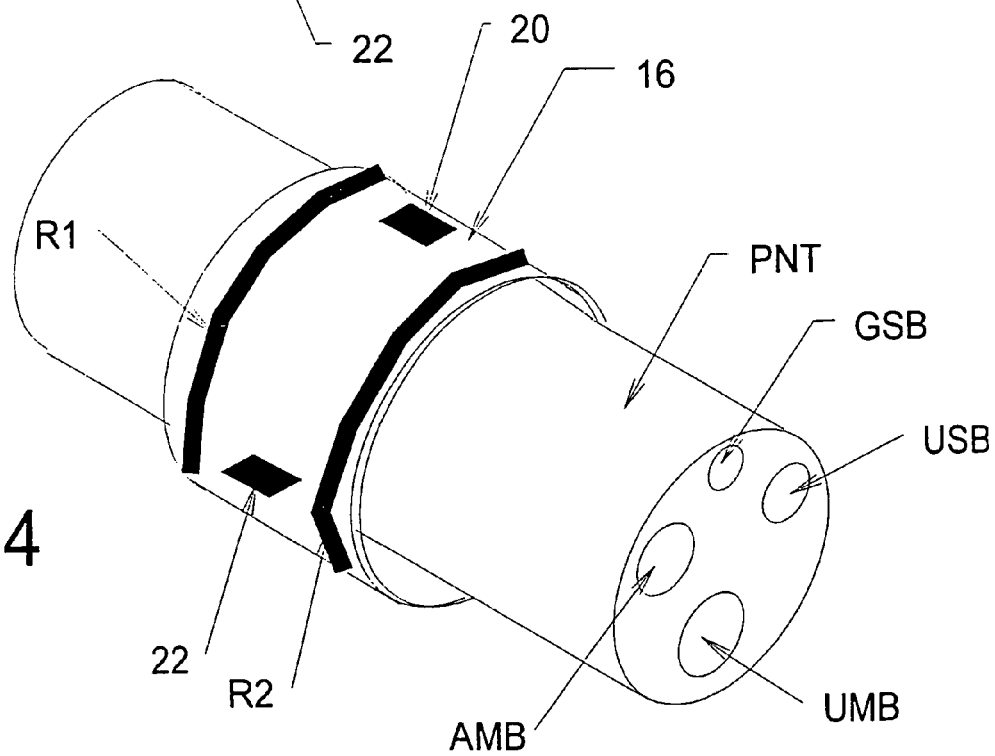

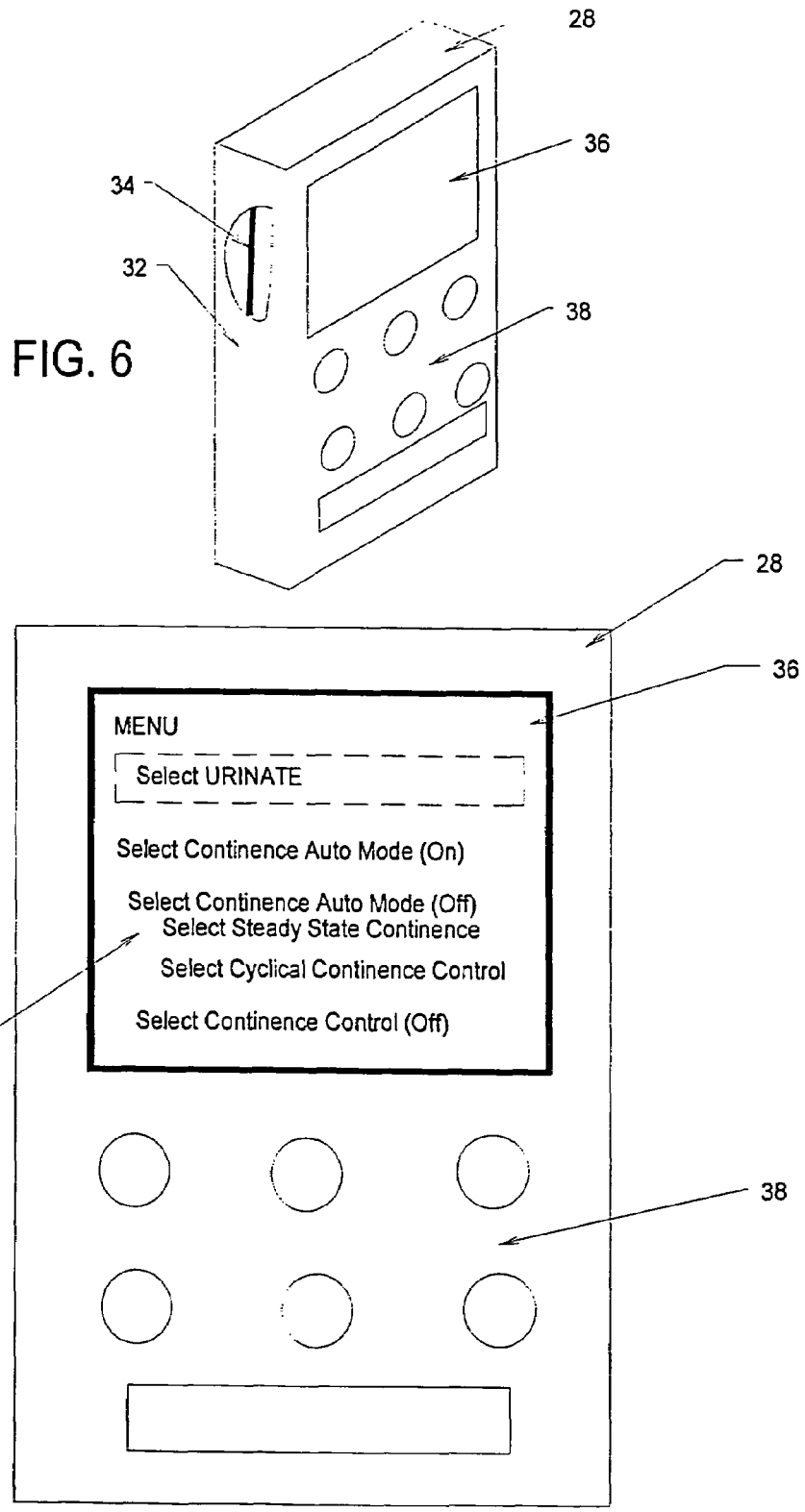

METHODS FOR SELECTIVELY STIMULATING COMPONENTS IN, ON, OR NEAR THE PUDENDAL NERVE OR ITS BRANCHES TO ACHIEVE SELECTIVE PHYSIOLOGIC RESPONSES

RELATED APPLICATIONS

This application is a divisional of application Ser. No. 10/113,828 filed 29 Mar. 2002, now U.S. Pat. No. 6,907,293 dated 14 Jun. 2005, which claims the benefit of U.S. Provisional Patent Application Ser. No. 60/280,222, filed Mar. 30, 2001, and entitled "Systems and Methods for Selectively Stimulating Fascicles in the Pudendal Nerve to Achieve Selective Physiologic Responses," which is incorporated herein by reference.

FIELD OF THE INVENTION

This invention relates to systems and methods for stimulating nerves in animals, including humans.

BACKGROUND OF THE INVENTION

The lower urinary tract comprises the bladder, urethra, periurethral muscles and sphincters, and accessory organs. The lower urinary tract has two primary functions: the accumulation and storage of urine (continence), and the elimination of urine at an appropriate time (micturition or urination).

In able-bodied individuals, continence is maintained by low-pressure urine storage in a highly compliant bladder, augmented by tonic activity in the internal and external urethral sphincters. Micturition is achieved in such individuals by synergic relaxation of the urethral sphincter and contraction of the bladder.

Supra-sacral spinal cord injury, brainstem stroke, or disease (e.g., multiple sclerosis) can break or otherwise disrupt the path or paths by which electrical signals generated by the brain normally travel to neuromuscular groups in the lower urinary tract and elsewhere in the body. As a result, even though these nerves and muscles are intact, abnormal electrical signals or no electrical signals are received from the spinal cord, and the associated muscles do not function.

In the lower urinary tract, paralysis of the bladder may occur, and, with it, the inability to empty the bladder voluntarily. Loss of bladder control is a major, devastating effect of these conditions.

These conditions can also result in bladder hyper-reflexia, in which the bladder contracts spontaneously at small fluid volumes. Bladder sphincter dysynergia can also occur, in which the external urethral sphincter contracts, rather than relaxes, during bladder contractions. Hyper-reflexia and dysynergia lead to bladder contraction with high pressure, impaired voiding, large post-void residual volumes, and low bladder compliance.

These dysfunctions often lead to ureteric reflux and obstruction, infection of the kidneys, episodes of autonomic dysreflexia with dangerous rises in blood pressure, incontinence that leads to skin problems, frequent urinary tract infections, and long term renal damage. Urological complications are one of the leading causes of morbidity in persons with spinal cord injury. Loss of bladder control also has profound social impact and leads to decreased quality of life. It also leads to large direct medical costs of procedures, supplies, and medications.

Clean self-catheterization, sometimes in combination with anticholinergic agents, is presently the most effective way to treat the neurogenic bladder. This treatment, however, requires individuals with dexterity for catheterization, as well as tolerance for and response to the anticholinergic agents. Even with these individuals, urinary tract infections persist.

Restoration of bladder evacuation and continence has been achieved by electrical stimulation of the sacral nerve roots, coupled with surgical transections of sacral sensory nerve roots (dorsal rhizotomy). The dorsal rhizotomy eliminates bladder hyper-reflexia and bladder-sphincter dysynergia. This technology has resulted in documented medical, quality of life, and financial benefits. However, widespread application of this technology is limited because of the irreversible effects of the dorsal rhizotomy (which leads to loss of reflex erection in males) and the complex surgical implant procedure itself (which requires access through the back along the spine, laminectomies of vertebral bodies, and the risk of cerebrospinal fluid leaks and intradural infections).

Other, physical conditions also have adverse affects on day-to-day bladder function. For example, a condition called urge incontinence, for which there is sometimes no neurological cause found, results in a hyperactive bladder and a loss of continence. There is also a condition called stress incontinence, which can arise after muscle is stretched in the pelvis during childbirth. Bladder instability or dysfunction are also chronic conditions of many elderly people, especially women. There is a need for systems and methods that can restore bladder and other urinary tract functions, e.g., micturition and/or continence, in a straightforward manner, without requiring self-catheterization, drug therapy, complicated surgical procedures, or irreversible surgical transections of nerve fibers. There is also a need for systems and methods that address dysfunctions or injuries affecting lower bowel functions (e.g., fecal incontinence and/or defecation) and/or sexual functions (e.g., erection of the penis, vaginal lubrication, ejaculation, and/or orgasm).

SUMMARY OF THE INVENTION

The invention provides systems and methods for stimulating selectively the components or fascicles of a mixed or compound nerve, to monitor, or control, or both monitor and control desired physiological functions. Selectivity among nerve components can include the selection among the components within a compound nerve trunk, or among branches of a nerve trunk, or between afferent (sensory) or efferent (motor) nerve fibers with a given nerve structure, or selection with regard to size of nerve fibers, or with regard to direction of activation, or with regard to the functions of nerve activation (resulting in the generation of an action potential or impulse and its propagation along a nerve) or nerve inactivation or block (resulting in prevention of activation or propagation of an action potential or impulse).

The systems and methods that embody features of the invention are generally applicable for use in conjunction with mixed or compound nerve structures throughout the body. For example, the systems and methods are well suited for use in conjunction with the pudendal nerve, and, in particular, the pudendal nerve trunk and its afferent and efferent branches or components away from the sacral root, that innervate muscles and organs in the lower urinary tract, lower bowel, and the genitals. The pudendal nerve trunk or its branches are spaced away from the sacral root and spinal column. They are accessible from the front of the body and do not require complicated surgical procedures on, in, or near the spinal column or entailing dorsal rhizotomy.

One aspect of the invention provides systems and methods for controlling a desired physiological function that involve placing at least one electrode on, in, or near a targeted component of the pudendal nerve away from a sacral root. The systems and methods apply an electrical signal to the electrode to stimulate selectively the targeted component, thereby affecting the desired physiological function.

The desired physiological function can vary. It can, for example, comprise controlling a lower urinary tract function, such as urinary incontinence or micturition, or both. As another example, the desired physiological function can comprise controlling a lower bowel function, such as fecal incontinence, or defecation, or peristalsis, or combinations thereof. As another example, the desired physiological function can comprise controlling a sexual function, such as erection, vaginal lubrication, ejaculation, or orgasm, or combinations thereof.

The systems and methods can achieve the desired physiological result by the selective stimulation of an afferent component of the pudendal nerve, or an efferent component of the pudendal nerve, or both, using a single electrode or a multiple electrode array. The selective stimulation can serve to activate selectively one or more components, or activate selectively one component while inactivating selectively another component, or inactivate selectively one or more components, or other combinations of activation and/or inactivation, to achieve the desired physiological result.

For example, the systems and methods can place the electrode on, in, or near a pudendal nerve branch, which can comprise, depending upon the desired function, either an afferent nerve branch, an efferent nerve branch, or both. In this arrangement, the electrode can comprise a single electrode or a multiple electrode array. The single electrode or the electrode array can be used in association with a pulse generator, to provide selective stimulation of the pudendal nerve branch, to achieve a desired physiological response.

Alternatively, or in combination, the systems and methods can place the electrode on, in, or near the pudendal nerve trunk. In this arrangement, the systems and methods can apply an electrical signal or signals to stimulate selectively an afferent component of the pudendal nerve trunk, or an efferent component of the pudendal nerve trunk, or both. In this arrangement, the electrode can comprise a multiple electrode array operated to achieve selective stimulation of targeted afferent component (s), or targeted efferent component(s), or both. The electrode array can be used in association with a pulse generator, to provide selective stimulation of individual components or fascicles within the pudendal nerve trunk, to achieve different physiological responses.

The systems and methods can apply the electrical signal(s) in response to a volitional act of an individual, or in response to sensed physiological events, or both. The systems and methods can also apply a pre-programmed pattern of electrical signals, either on demand or in response to sensed physiological events. The physiological events can be sensed by the placement of at least one recording electrode in, on, or near a nerve, e.g., the pudendal nerve trunk or a branch or component of the pudendal nerve.

This aspect of the invention provides systems and methods involving the pudendal nerve, which are capable of evoking desirable physiological responses in persons who lack the ability to otherwise produce these responses—e.g., maintain urinary continence and/or produce micturition, and/or maintain fecal incontinence and/or produce defecation, and/or maintain normal male/female sexuality responses.

For example, a micturition response (increase in bladder pressure and reduction in activity in the external urethral sphincter) can be evoked by selective stimulation of a urethral afferent component of the pudendal nerve (e.g., to cause bladder contractions, or affect voluntary urinary sphincter function, or both), an efferent component of the pudendal nerve (e.g., to affect voluntary urinary sphincter function), or both. For a micturition response, selective stimulation of an efferent component can be undertaken to affect nerve inactivation, causing relaxation of the urinary sphincter, thereby facilitating micturition. This may undertaken alone or be combined with selective stimulation of an afferent component to affect nerve activation, causing bladder contraction, further promoting micturition. Selective stimulation of an afferent component alone to affect nerve activation, causing bladder contraction, can also promote micturition.

A continence response (arresting bladder contractions) can be evoked by selective stimulation of a genital afferent component of the pudendal nerve (to inhibit bladder contractions), an efferent component of the pudendal nerve (to affect nerve activation for voluntary urinary sphincter function), or both. For a continence response, selective stimulation of either or both afferent or efferent components can be undertaken to affect nerve activation to evoke the desire physiological responses.

As other examples, a defecation response (increase in contraction of the rectum and reduction in activity in the external anal sphincter) can be evoked by selective stimulation of an afferent component of the pudendal nerve (to cause contractions of the rectum, or affect voluntary anal sphincter function, or both), an efferent component of the pudendal nerve (to affect voluntary anal sphincter function), or both. For a defecation response, selective stimulation of an efferent component can be undertaken to affect nerve inactivation, causing relaxation of the anal sphincter, thereby facilitating defecation. This may be undertaken alone or be combined with selective stimulation of an afferent component to affect nerve activation, causing contraction of the rectum, further promoting defecation. Selective stimulation of an afferent component alone to affect nerve activation, causing contraction of the rectum, can also promote defecation.

A fecal continence response (arresting contractions of the rectum and affecting activity of the voluntary anal sphincter) can be evoked by selective stimulation of an afferent component of the pudendal nerve (to inhibit contractions of the rectum), an efferent component of the pudendal nerve (to affect voluntary anal sphincter function), or both. For a fecal continence response, selective stimulation of either or both afferent or efferent components can be undertaken to affect nerve activation to evoke the desire physiological responses.

A response for controlling peristalsis (contraction of the colon) can be evoked by selective stimulation of one or more afferent components of the pudendal nerve. For peristalsis, selective stimulation of either or both afferent or efferent components can be undertaken to affect nerve activation to evoke the desire physiological responses.

As other examples, an erection response in males or a vaginal lubrication response in females may be evoked by the selective stimulation of an afferent component of the pudendal nerve—alone or in combination with other afferent components of the nervous system (e.g., ventral genital)—to affect dilation of blood vessels in the penis or lubrication in the vagina. An ejaculation response may be evoked by the selective stimulation of an afferent component of the pudendal nerve, or an efferent component of the pudendal nerve, or both—alone or in combination with other afferent components of the nervous system (e.g., ventral genital) and/or other efferent components of the nervous system—to contract pelvic muscles and cause ejaculation. An orgasm response may be evoked by the selective stimulation of an afferent component of the pudendal nerve—alone or in combination with other afferent components (e.g., ventral genital) and other components of the central nervous system.

In all the above examples, stimulation can be evoked automatically, or manually by a volitional act of the user. The stimulation can involve the use of pre-programmed pattern of stimulation signals.

Another aspect of the invention provides systems and methods for monitoring function of the lower urinary tract, or the lower bowel, or both. The systems and methods place at least one recording electrode sized and configured to be located on, in, or near a targeted component of the pudendal nerve to sense electrical activity relating, respectively, to bladder function or lower bowel function. The systems and methods generate an informational signal based upon the electrical activity sensed by the recording electrode.

In the case of bladder function, the informational signal can relate, e.g., to bladder contraction, bladder volume, or onset of bladder contraction. In the case of lower bowel function, the informational signal can relate, e.g., to contraction of the rectum, volume of the rectum, or onset of contraction of the rectum.

The component targeted by the recording electrode can comprise an afferent component of the pudendal nerve, an efferent component of the pudendal nerve, or both.

In one arrangement, the systems and methods locate the recording electrode on, in, or near a targeted branch of the pudendal nerve. The targeted branch can be an afferent branch, an efferent branch, or both.

Alternatively, or in combination, the systems and methods place the recording electrode on, in, or near the pudendal nerve trunk. In this arrangement, the component targeted by the recording electrode can comprise an afferent component of the pudendal nerve trunk, an efferent component of the pudendal nerve trunk, or both.

According to another aspect of the invention, the systems and methods generate a control signal affecting, respectively, bladder function or lower bowel function based, at least in part, upon the informational signal generated. In the case of bladder function, the control signal can either inhibit bladder contractions (evoking urinary continence) or cause bladder contraction (evoking micturition). In the case of lower bowel function, the control signal can either inhibit lower bowel function (evoking fecal continence) or cause lower bowel function (evoking defecation).

In one arrangement, the control signal is applied to an electrode located on, in, or near a targeted component of the pudendal nerve, in the manner already described.

For example, in the monitoring and control of bladder function, the onset of bladder contractions can be detected by recording electrical activity in the pudendal nerve. When detected, the informational signal is generated, and stimulation of a genital afferent component of the pudendal nerve, an efferent component of the pudendal nerve, or both can occur automatically, to arrest the contractions and affect function of the voluntary urethral sphincter. Alternatively, the user can manually initiate the stimulation of a genital afferent component of the pudendal nerve, an efferent component of the pudendal nerve, or both to evoke continence on demand. Likewise, the user can manually initiate the stimulation of a urethral afferent component of the pudendal nerve, an efferent component of the pudendal nerve, or both to evoke micturition on demand.

For example, in the monitoring and control of lower bowel function, the onset of contractions in the rectum can be detected by recording electrical activity in the pudendal nerve. When detected, the informational signal is generated, and stimulation of an afferent component of the pudendal nerve, an efferent component of the pudendal nerve, or both can occur automatically, to arrest the contractions and affect function of the voluntary anal sphincter. Alternatively, the user can manually initiate the stimulation of an afferent component of the pudendal nerve, an efferent component of the pudendal nerve, or both to evoke fecal continence on demand. Likewise, the user can manually initiate the stimulation of an afferent component of the pudendal nerve, an efferent component of the pudendal nerve, or both to evoke defecation on demand.

Other features and advantages of the inventions are set forth in the following specification and attached drawings.

BRIEF DESCRIPTION OF THE DRAWINGS

FIG. 3 is an enlarged cross sectional view of the pudendal nerve, as shown in FIG. 2, in association with a multiple electrode cuff that embodied features of the invention positioned about the pudendal nerve trunk;

FIG. 4 is a perspective side view of the pudendal nerve and multiple electrode cuff shown in FIG. 3;

FIG. 6 is view of a manual controller that can be used in association with the system shown in FIG. 5, the manual controller including a microprocessor that enables a user interface; and FIG. 7 is a view of a portion of the user interface that the manually controller shown in FIG. 6 can present to enable selection of different physiologic response using the system shown in FIG. 5.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

The various aspects of the invention will be described in connection with achieving the detection of nerve activity within and/or stimulation of targeted nerve components or fascicles within complex or compound nerve structures throughout the body. For the purpose of illustration, the invention will be disclosed in the context of the compound pudendal nerve trunk or its branches located away from the sacral root, to achieve desired physiological results in the lower urinary tract, and/or the lower bowel, and/or genital regions. That is because the features and advantages that arise due to the invention are well suited to this purpose. Still, it should be appreciated that the various aspects of the invention can be applied elsewhere in the body to achieve other objectives as well.

I. Anatomy of the Compound Pudendal Nerve Trunk

Figure 1:
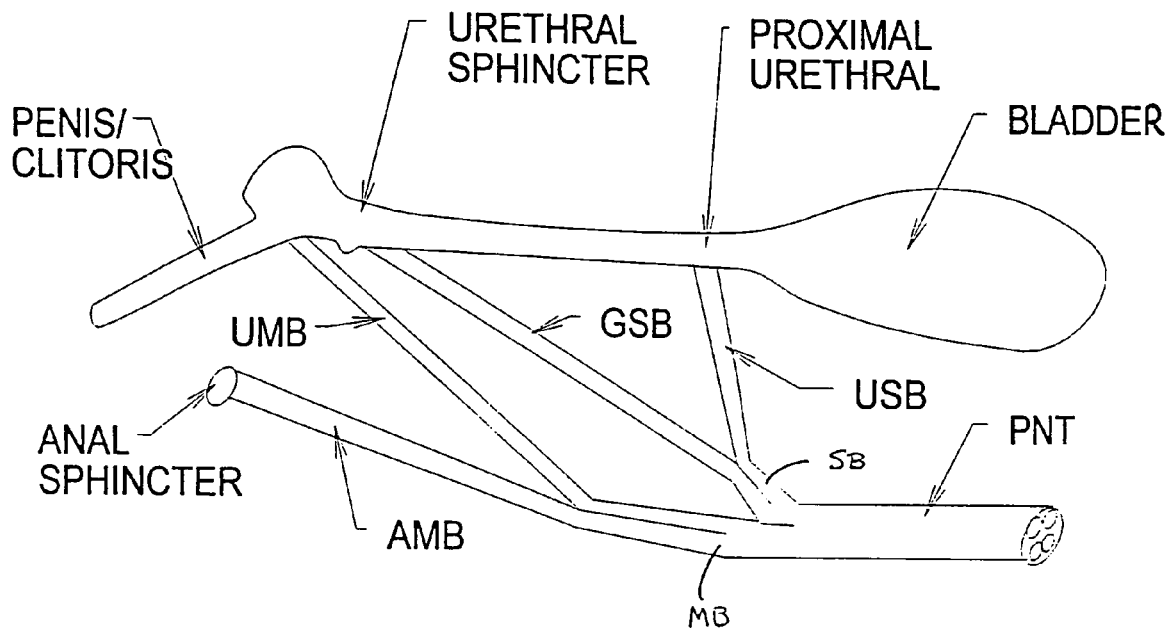
FIG. 1 is a schematic view of the lower urinary tract and the pudendal nerve that innervates the organs and muscles of the lower urinary tract.

The pudendal nerve trunk (PNT) carries afferent (sensory) and efferent (motor) nerve components that innervate muscles and organs in the lower urinary tract. FIG. 1 shows, in schematic form, the major branches of the pudendal nerve trunk (PNT). These major branches comprise the principal sensory (afferent) branch (SB) and the principal motor (efferent) branch (MB).

Extending from the principal sensory branch are the genital sensory branch (GSB) and the urethral sensory branch (USB). The genital sensory branch (GSB) comprises the dorsal nerve of the penis in males and the clitoral nerve in females. The urethral sensory branch (USB) innervates the urethra.

Extending from the principal motor branch are the external urethral sphincter branch (UMB), which innervates the external urethral sphincter, and the external anal sphincter branch (AMB), which innervates the external anal sphincter.

Research has indicated that the electrical activity of the pudendal nerve is modulated during bladder contractions. Thus electrical activity of the pudendal nerve can be used to detect the onset of bladder contractions. As just explained, the pudendal nerve innervates the muscles of the pelvic floor, including the external (voluntary) urethral sphincter and the external (voluntary) anal sphincter. In humans, increases in bladder pressure evoked by rapid injections of fluid into the bladder evoke an increase in activity of muscles of the pelvic floor. Following spinal injury, bladder-sphincter dysynergia leads to increases in pelvic floor bladder contractions. These data indicate that electrical recording of activity in the pudendal nerve or its branches will detect reflexive bladder contractions.

Research has also shown that electrical stimulation of the genital sensory branch (GSB) of the pudendal nerve inhibits bladder contractions. These data indicate that electrical stimulation of the GSB can abolish hyper-reflexive bladder contractions and increase bladder capacity in individuals with bladder hyper-reflexia due, e.g., to spinal injury.

Traditional views hold that coordinated micturition (bladder contractions coupled with a reduction in activity of the external urethral sphincter) requires a spinal-brainstem-spinal reflex loop that is triggered by bladder distension. However, bladder contractions can also be evoked by activation of urethral afferents. The data indicates that stimulation of the urethral sensory nerve branch (USB) will evoke a micturition-like bladder contraction and a reduction in activity in the urethral sphincter. This combination will lead to low-pressure continuous stream evacuation of the bladder on demand.

Figure 2:
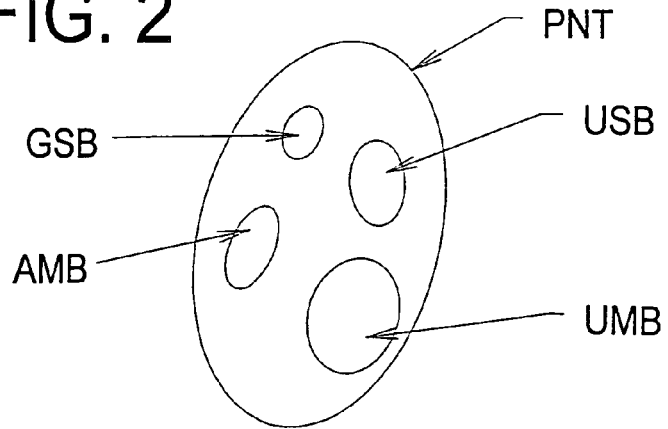
FIG. 2 is a schematic cross sectional view of the pudendal nerve, showing the peripherally separated fascicles that occupy the main nerve trunk, comprising different efferent and afferent nerve branches.

A cross section of the pudendal nerve trunk (PNT) (see FIG. 2) shows that the major motor and sensory nerve branches just described are located in peripherally spaced-apart components or fascicles in the nerve trunk (PNT). This nerve geometry lends itself to the use of a peripherally spaced cuff array 16 of electrodes 18, 20, 22, 24 (see FIGS. 3 and 4) implanted in, on, or near the pudendal nerve trunk (PNT) to affect independent neural sensing and/or neural stimulation of the nerve fascicles of the pudendal nerve trunk (PNT).

FIGS. 3 and 4 show the array 16 as comprising four electrodes 18, 20, 22, and 24 spaced apart at regular ninety-degree intervals. In the illustrated embodiment, the array 16 also includes two ring return electrodes R1 and R2 at each end of the cuff. The array 16 can comprise a greater or lesser number of electrodes 18, 20, 22, and 24, and the spacing among the electrodes 18, 20, 22, and 24 can differ and need not be uniform.

The array 16 is desirably implanted without prior reference to the particular fascicular structure of the nerve, leading to a random orientation between electrodes and fascicles. Thus, programming or "tuning" will be required by a clinician to ascertain positions and operating parameters of electrodes 18 to 24 in the array 16 to bring about the desired stimulation of individual targeted fascicles. Further details of the programming or "tuning," of the array 16 prior to use will be described in greater detail later. Alternatively, separate electrodes could be implanted in, on, or near the individual branches, thereby avoiding a random orientation. Techniques enabling sub-fascicular selection could also be employed.

II. System Overview

Figure 5:
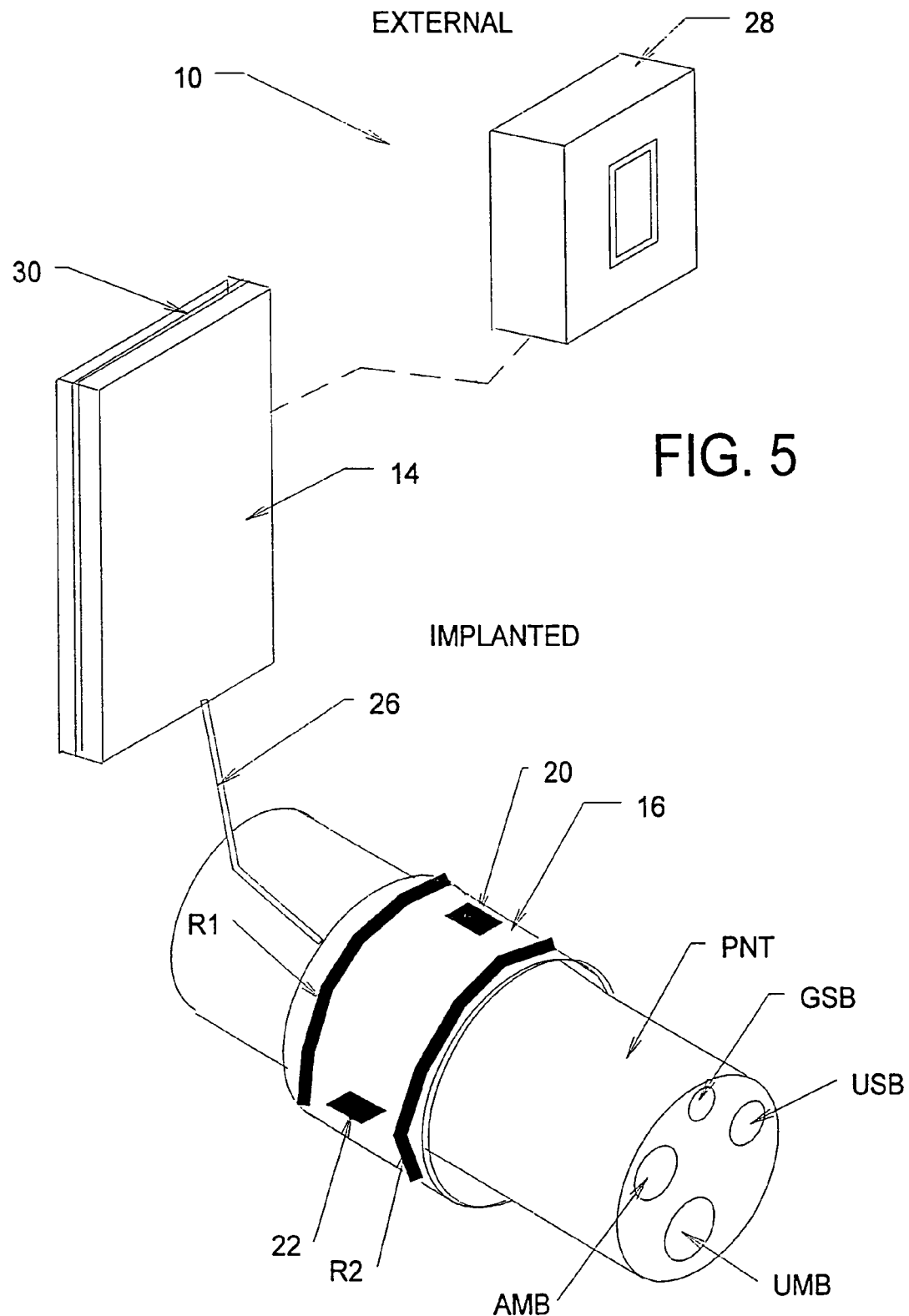
FIG. 5 is a schematic view of a system, which is coupled to the multiple electrode cuff shown in FIGS. 3 and 4, and which provides selective stimulation of individual fascicles within the pudendal nerve, to achieve different physiologic responses, e.g., continence and micturition.
Figure 5:
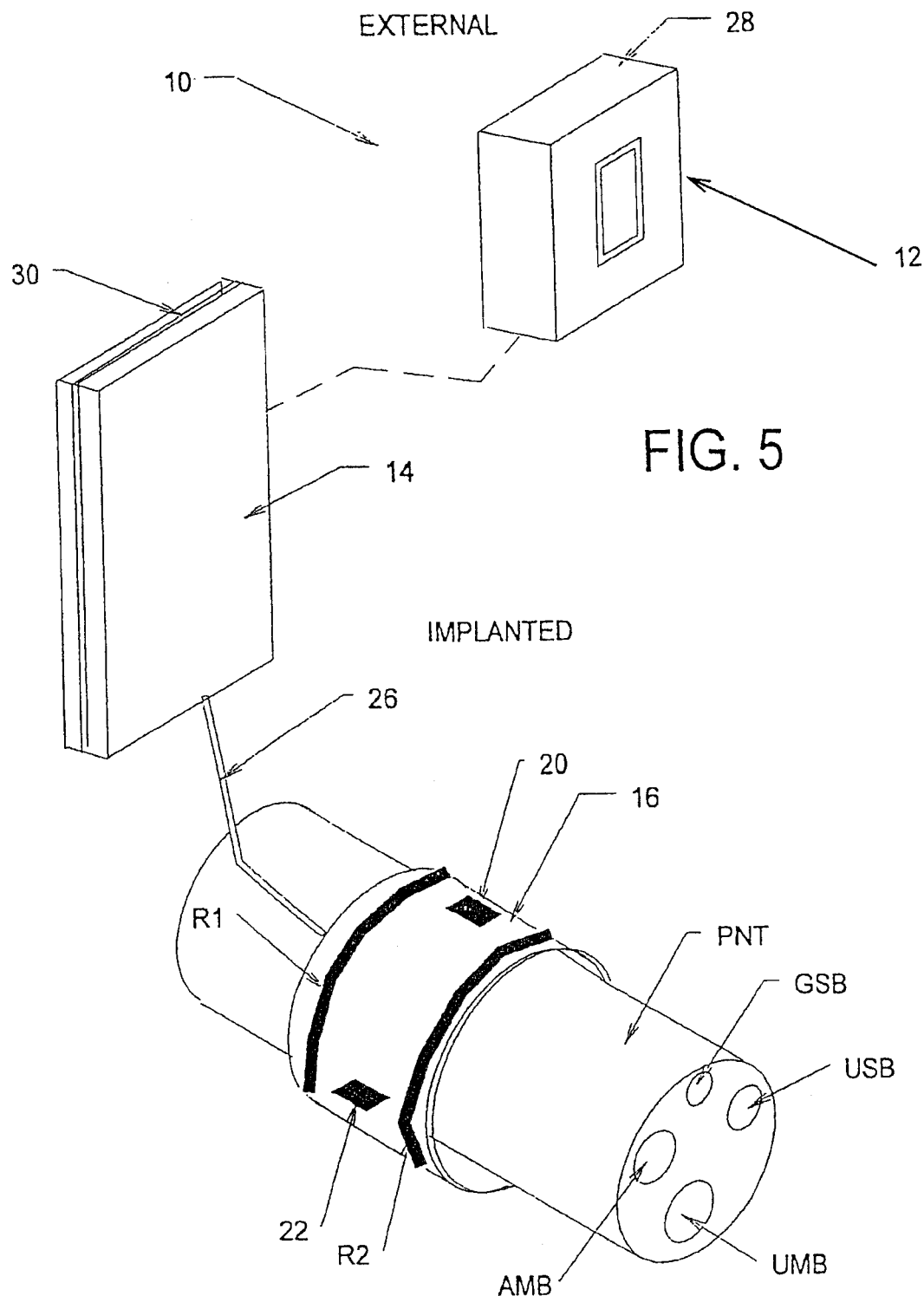

FIG. 5 shows a system 10 that makes possible the detection of neural impulses and/or the stimulation of targeted nerve branches within the compound pudendal nerve trunk (PNT).

The system 10 can generate and distribute electrical stimulus waveforms to selected afferent and/or efferent nerve fascicles in the nerve trunk (PNT), or to selected afferent and/or efferent branches outside the nerve trunk (PNT).

As shown, the system 10 comprises four basic functional components including (i) one or more control signal sources 12; (ii) a pulse generator 14; (iii) at least one electrode 18; and (iv) electrical leads 26 that couple the electrode 18 to the pulse generator 14.

As assembled and arranged in FIG. 5, the control signal sources 12 function to generate prescribed response demand inputs to the pulse generator 14. The prescribed demand inputs are associated with desired physiologic response(s), as will be described in greater detail later.

The pulse generator 14 may include an on-board, programmable microprocessor 30, which carries embedded code. The code expresses pre-programmed rules or algorithms under which the desired electrical stimulation waveform is generated and distributed to the electrode array 16 in response to the prescribed demand inputs. According to these programmed rules, the pulse generator 14 directs prescribed stimulation waveforms through the leads 26 to the electrode 18 or electrodes 18 to 24 in the electrode array 16 that stimulate selectively the targeted fascicle associated with the desired response. The electrode selection parameters and operating parameters for a given demand input are preprogrammed into the code by a clinician, as will be described later. In this way, the particular physiologic response associated with a particular prescribed demand input is reliably achieved.

The stimulation waveform generated is desirable low frequency, e.g., less than about 10 Hz. The frequency can be tuned to achieve the desired physiological result. The shape of the waveform can also vary. It can, e.g., be a typical square pulse, or possess a ramped shape. The pulse, or the rising or falling edges of the pulse, can present various linear, exponential, hyperbolic, or quasi-trapezoidal shapes. As will be described later, the stimulation waveform can be continuous, or it can be variable and change cyclically or in step fashion in magnitude and waveform over time.

As thus described, the system 10 is operable for controlling a physiological function. The system 10 includes at least one electrode 18 sized and configured to be located on, in, or near a targeted component of the pudendal nerve away from a sacral root. The pulse generator 14 coupled to the electrode applies an electrical signal to stimulate selectively the targeted component of the pudendal nerve, to achieve the desired physiologic function.

The targeted component can comprise an afferent component of the pudendal nerve, or an efferent component of the pudendal nerve, or both. As shown in FIG. 5, the electrode takes the form of a multiple electrode array 16 that is sized to be located on, in, or near the pudendal nerve trunk (PNT). In this arrangement, as will be described in greater detail later, the pulse generator 14 is able to stimulate selectively an afferent component in the nerve trunk, or an efferent component in the nerve trunk, or both, to achieve the desired physiological function.

Alternatively, a single electrode 18 or an array of electrodes 18 to 24 like that shown in FIG. 5 can be sized and configured to be located on, in, or near a pudendal nerve branch, outside the nerve trunk. The nerve branch can comprise an afferent branch, or efferent branch, or both. In this arrangement, the pulse generator 14 is able to stimulate selectively an afferent branch of the nerve trunk, or efferent branch of the nerve trunk, or both, to achieve the desired physiological function.

As will be described in greater detail later, the pulse generator 14 can be operated to apply the electrical signal(s) in response to a volitional act of an individual. Due to the microprocessor 30, the pulse generator 14 can be, if desired, operated to apply a pre-programmed pattern of electrical signals.

The system 10 can also include at least one recording electrode located in, on, or near a nerve to sense electrical events. As illustrated, the electrode serves to detect electrical activity within the pudendal nerve trunk (PNT), and, in particular, within the efferent external anal sphincter branch (AMB) and/or efferent urethral sphincter branch (UMB) of the pudendal nerve trunk (PNT). This electrical activity can be correlated with the onset of bladder contractions and/or contractions of the rectum. In this arrangement, the pulse generator 14 can be coupled to the recording electrode and operated to apply the electrical signal in response to the sensed electrical events.

The system 10 can be configured and operated in association with the pudendal nerve trunk or its branches to achieve various desired physiological functions. The system 10 can, for example, be configured and operated to control one or more lower urinary tract functions, such as urinary incontinence, and/or micturition, or both. As another example, the system 10 can be configured and operated to control one or more lower bowel functions, such as fecal incontinence, and/ or defecation, or peristalsis, or combinations thereof. As yet another example, the system 10 can be configured and operated to control one or more sexual functions, such as (in males) erection, and/or ejaculation, and/or orgasm, or (in females) vaginal lubrication and/or orgasm.

The configuration and operation of the system 10 to achieve these various physiological functions will now be described in greater detail.

III. Lower Urinary Tract Functions

The system 10 can generate and distribute stimulus waveforms to the fascicle of the afferent genital sensory branch (GSB) of the pudendal nerve trunk (PNT), or the fascicle of the urethral efferent branch (UMB), or both. The stimulation of the afferent component inhibits bladder contractions. The stimulation of the efferent component affects voluntary urinary sphincter function. Alone, or in tandem, the stimulation can serve to arrests bladder contractions (including those of a nascent hyper-reflexive type), and/or affect urinary sphincter function. The system 10 can thereby control urinary continence.

The system 10 can also generate and distribute electrical stimulus waveforms to the fascicle of the afferent urethral sensory branch (USB) of the pudendal nerve trunk (PNT), or the fascicle of the urethral efferent branch (UMB), or both. The stimulation of the afferent component produces bladder evacuation. The stimulation of the efferent component affects voluntary urinary sphincter function. Alone, or in tandem, the stimulation can achieve micturition on demand.

In the illustrated embodiment, neural recording and stimulation are carried out by the array of multiple, circumferentially spaced electrodes 18 to 24 placed near, on, or in the pudendal nerve trunk (PNT), shown in FIGS. 3 and 4. Of course, individual electrodes or multiple electrode arrays located in, on or near the genital afferent branch (GSB) and/or the urethral afferent branch (USB) and/or urethral efferent branch (UMB) could be used.

According to pre-programmed rules expressed by the code embedded in the microprocessor 30, the pulse generator 14 directs prescribed stimulation waveforms through the leads 26 to the electrode 18 or electrodes 18 to 24 in the array 16 that stimulate the targeted fascicle associated with the desired response, e.g., the afferent genital sensory branch (GSB) and/or the efferent urethral branch (UMB) (for continence) or the afferent urethral sensory branch (USB) and/or the efferent urethral branch (UMB) (for micturition).

A continence response (arresting bladder contractions) can be evoked by selective stimulation of a genital afferent component of the pudendal nerve (to inhibit bladder contractions), an efferent component of the pudendal nerve (to affect nerve activation for voluntary urinary sphincter function), or both. For a continence response, selective stimulation of either or both afferent or efferent components can be undertaken to affect nerve activation to evoke the desire physiological responses.

The microprocessor code can also express rules or algorithms pre-programmed by a clinician, under which electroneurogram (ENG) activity in the whole pudendal nerve trunk (PNT), or the individual efferent external anal sphincter branch (AMB) and/or efferent urethral sphincter branch (UMB) of the nerve trunk (PNT), are characterized to generate an information signal. The informational signal can relate, e.g., to bladder contraction, or bladder volume, or onset of bladder contraction. The informational signal can be expressed in a user-readable output, to provide feedback to the user or clinician as to the state of bladder function. As will be described later, the informational signal can also be used as a control, to lead to the automatic generation of a demand input.

In the illustrated implementation, the pulse generator 14 is programmed to respond to one or more prescribed continence demand inputs to affect, e.g., an arrest of nascent hyper-reflexive bladder contractions (thereby achieving continence). In response to the one or more prescribed continence demand inputs, the pulse generator 14 applies electrical waveforms to the electrode 18 or electrodes 18 to 24 in the array 16 that are positioned to stimulate the afferent genital sensory branch (GSB) and/or the efferent urethral motor branch (UMB) of the pudendal nerve trunk (PNT).

In the illustrated embodiment, the pulse generator 14 is also programmed to respond to one or more prescribed micturition demand inputs to affect bladder evacuation (thereby achieving micturition). In response to the one or more prescribed micturition demand inputs, the pulse generator 14 applies electrical waveforms to the electrode 18 or electrodes 18 to 24 in the array 16 that are positioned to stimulate the afferent urethral sensory branch (USB) and/or the efferent urethral motor branch (UMB) of the pudendal nerve trunk (PNT).

A micturition response (increase in bladder pressure and reduction in activity in the external urethral sphincter) can be evoked by selective stimulation of a urethral afferent component of the pudendal nerve (e.g., to cause bladder contractions, or affect voluntary urinary sphincter function, or both), an efferent component of the pudendal nerve (e.g., to affect voluntary urinary sphincter function), or both. For a micturition response, selective stimulation of an efferent component can be undertaken to affect nerve inactivation, causing relaxation of the urinary sphincter, thereby facilitating micturition. This may undertaken alone or be combined with selective stimulation of an afferent component to affect nerve activation, causing bladder contraction, further promoting micturition. Selective stimulation of an afferent component alone to affect nerve activation, causing bladder contraction, can also promote micturition.

A given control signal source 12 can be configured to generate the demand inputs automatically, without volitional act by the user. A given control signal source 12 can also be configured to generate the demand inputs manually, thereby requiring a volitional act by the user. The system 10 can rely upon either or both forms of control signal sources 12.

Using these configurations, stimulation to achieve continence can be either unconditional or conditional. Unconditional stimulation is applied continuously, except when stopped by a manual signal. Conditional stimulation occurs in discrete intervals triggered by a manual or automatic (e.g. neural recoding) signal.

For example, one form of an automatic control signal source 12 can comprise one or more electrodes 18 to 24 in the array 16 that are positioned to sense electroneurogram (ENG) activity in the whole pudendal nerve, or in individual efferent external anal sphincter branch (AMB) and/or efferent urethral sphincter branch (UMB). The recording can comprise a whole nerve recording, with the neural signal recorded being an aggregate of the activity of all nerve fibers in the pudendal nerve (PNT). However, the whole nerve recording is typically dominated by signals arising from the largest diameter fibers, which comprise the AMB and UMB. Alternatively, the recording can comprise a selective recording from the individual branches AMB and UMB. Regardless, the recorded activity is processed by the pulse generator 14 to detect the onset of hyper-reflexive bladder contractions.

When the onset is detected by the pulse generator 14, a demand input is automatically transmitted. The pulse generator 14, in turn, automatically generates the desired waveforms to stimulate the afferent genital sensory branch (GSB) and/or the efferent urethral motor branch (UMB), to thereby arrest the hyper-reflexive contractions and/or affect voluntary urinary sphincter function, and thereby maintain continence.

One form of a manual control signal source 12 can comprise an external controller 28 that the user manipulates. The external controller can take the form of a remote control switching device or magnetic reed switch. The manual controller 28 can be used in the place of or in combination with the ENG sensing electrodes or other form of automatic signal source 12.

For example, using the manual controller 28, the user can generate a continence demand input, independent or in the absence of any automatic continence demand input. In response, the pulse generator 14 applies electrical waveforms to the electrode 18 or electrodes 18 to 24 in the array 16 that are positioned to stimulate the afferent genital sensory branch (GSB) and/or efferent urethral motor branch (UMB) of the pudendal nerve trunk (PNT). Using the manual controller 28, the user can also terminate a continence demand input. As a result, the user is able to "turn on" or "turn off" continence control, depending, e.g., upon the time of day or fluid consumption. Using a manual controller 28, the user can also enable or disable an automatic continence demand input source.

As another example, using a manual controller 28, the user can initiate a micturition demand input on their own volition. In response, the pulse generator 14 applies electrical waveforms to the electrode 18 or electrodes 18 to 24 in the array 16 that are positioned to stimulate the afferent urethral sensory branch (USB) and/or the efferent urethral motor branch (UMB) of the pudendal nerve trunk (PNT). As a result, the user is able to urinate on demand.

As shown in FIG. 6, the manual controller 28 can be housed in a compact, lightweight, hand held housing 32, which desirable includes its own microprocessor 34 powered by a rechargeable, onboard battery (not shown). The microprocessor 34 carries embedded code which may include pre-programmed rules or algorithms that may govern operation of a display 36 and keypad 38, to create a user interface. The microprocessor 34 also expresses pre-programmed rules or algorithms under which desired demand inputs are selected and generated using the display 36 and the keypad 38. The microprocessor 34 can also have the capability to log data, and thereby keep a record of detection and stimulation that can be assessed by a physician. Further details of a controller 28 of this type will be described later.

The basic functional components can be constructed and arranged in various ways. In one representative implementation, the electrode array 16, leads 26, and pulse generator 14 are all implanted. In this arrangement, the manual controller 28 comprises an external unit that is, e.g., magnetically coupled to the pulse generator 14, or coupled by a radio frequency link to the pulse generator 14 (e.g., in the manner as described in Peckham et al U.S. Pat. No. 5,167,229, which is incorporated herein by reference). Alternatively, a manual controller 28 can be coupled by percutaneous leads to the pulse generator 14.

IV. Lower Bowel Functions

In another embodiment, the system 10 can be configured and operated to generate and distribute stimulus waveforms selectively to one or more targeted components of the pudendal nerve trunk (PNT) to control lower bowel functions.

In one embodiment, the system 10 can be configured and operated to control fecal incontinence. In this arrangement, the system 10 include at least one electrode 18 sized and configured to be located on, in, or near a targeted component of the pudendal nerve away from a sacral root. The pulse generator 14 is coupled to the electrode 18 to apply an electrical signal to stimulate selectively the targeted component. The targeted component can comprise an afferent component of the pudendal nerve identified by a clinician to inhibit rectal contractions, or an efferent component identified by a clinician to affect voluntary anal sphincter function, or both. The electrode can comprise a single electrode 18 or the multiple electrode array 16 of the type shown in FIGS. 3 and 4.

A fecal continence response (arresting contractions of the rectum and affecting activity of the voluntary anal sphincter) can be evoked by selective stimulation of an afferent component of the pudendal nerve (to inhibit contractions of the rectum), an efferent component of the pudendal nerve (to affect voluntary anal sphincter function), or both. For a fecal continence response, selective stimulation of either or both afferent or efferent components can be undertaken to affect nerve activation to evoke the desire physiological responses.

In another embodiment, the system 10 can be configured and operated to control defecation. In this arrangement, the system 10 includes at least one electrode 18 sized and configured to be located on, in, or near a targeted component of the pudendal nerve away from a sacral root. The pulse generator 14 is coupled to the electrode 18 to apply an electrical signal to stimulate selectively the targeted component. The targeted component can comprise an afferent component of the pudendal nerve identified by a clinician to cause rectal contractions, or an efferent component identified by a clinician to affect voluntary anal sphincter function, or both. As before, the electrode can comprise a single electrode 18 or the multiple electrode array 16 of the type shown in FIGS. 3 and 4.

A defecation response (increase in contraction of the rectum and reduction in activity in the external anal sphincter) can be evoked by selective stimulation of an afferent component of the pudendal nerve (to cause contractions of the rectum, or affect voluntary anal sphincter function, or both), an efferent component of the pudendal nerve (to affect voluntary anal sphincter function), or both. For a defecation response, selective stimulation of an efferent component can be undertaken to affect nerve inactivation, causing relaxation of the anal sphincter, thereby facilitating defecation. This may be undertaken alone or be combined with selective stimulation of an afferent component to affect nerve activation, causing contraction of the rectum, further promoting defecation. Selective stimulation of an afferent component alone to affect nerve activation, causing contraction of the rectum, can also promote defecation.

In either arrangement, single or multiple electrodes may be located on, in, or near the selected afferent branch of the pudendal nerve; or on, in, or near the selected efferent branch of the pudendal nerve; or both. Alternatively, a multiple electrode array 16 may be sized and configured to be located on, in, or near the pudendal nerve trunk, as FIG. 4 shows.

In this arrangement, to control fecal incontinence, the pulse generator 40 is coupled to the electrode array 16 to apply an electrical signal to stimulate selectively the afferent component of the pudendal nerve trunk that has been identified by the clinician to inhibit rectal contractions, or an efferent component of the pudendal nerve trunk that has been identified by the clinician to affect voluntary anal sphincter function, or both. Likewise, to control defecation, the pulse generator 40 is coupled to the electrode array 16 to apply an electrical signal to stimulate selectively an afferent component of the pudendal nerve trunk that has been identified by the clinician to cause rectal contractions, or an efferent component of the pudendal nerve trunk that has been identified by the clinician to affect voluntary anal sphincter function, or both.

As before explained in connection with the control of lower urinary tract functions, in controlling lower bowel functions, the pulse generator 14 can operate to apply the electrical signal in response to a volitional act of an individual. According to the pre-programmed rules expressed by the code embedded in the microprocessor 30, the pulse generator 14 directs prescribed stimulation waveforms through the leads 26 to those electrode or electrodes 18 to 24 in the array 16 that stimulate the targeted fascicle associated with the desired response, e.g., fecal continence or defecation.

As also previously explained, the system 10 can include at least one recording electrode located in, on, or near the pudendal nerve or a branch of the pudendal nerve to sense electrical events indicative of rectal function. In this arrangement, the pulse generator 14 is coupled to the recording electrode and operates to apply the electrical signal in response to the sensed electrical events.

More particularly, the microprocessor code of the pulse generator 14 can express rules or algorithms pre-programmed by a clinician, under which electroneurogram (ENG) activity in the whole pudendal nerve trunk (PNT), or the individual efferent external anal sphincter branch (AMB) and/or efferent urethral sphincter branch (UMB) of the nerve trunk (PNT), are characterized to provide an informational signal. The informational signal can relate, e.g., to the state of rectal contraction, rectal volume, or onset of rectal contraction. The informational signal can be expressed in a user-readable output, to provide feedback to the user or clinician as to the state of lower bowel function. As will be described later, the informational signal can be used as a control, to lead to the automatic generation of a demand input.

In the illustrated implementation, the pulse generator 14 is programmed to respond to one or more prescribed continence demand inputs to affect an arrest of rectal contractions and/or affect voluntary anal sphincter function (thereby achieving continence). In response to the one or more prescribed continence demand inputs, the pulse generator 14 applies electrical waveforms to the electrode or electrodes 18 to 24 in the array 16 that are positioned to stimulate the selected afferent component of the pudendal nerve trunk (PNT)—to inhibit contractions of the rectum—and/or the selected efferent component of the pudendal nerve trunk (PNT)—to affect voluntary anal sphincter function.

In the illustrated embodiment, the pulse generator 14 can also be programmed to respond to one or more prescribed defecation demand inputs to affect defecation. In response to the one or more prescribed defecation demand inputs, the pulse generator 14 applies electrical waveforms to the electrode or electrodes 18 to 24 in the array 16 that are positioned to stimulate the selected afferent component of the pudendal nerve trunk (PNT)—to cause rectal contractions—and/or the selected efferent component of the pudendal nerve trunk (PNT)—to affect voluntary anal sphincter function.

A given control signal source 12 can be configured to generate the demand inputs automatically, without volitional act by the user. A given control signal source 12 can also be configured to generate the demand inputs manually, thereby requiring a volitional act by the user. The system 10 can rely upon either or both forms of control signal sources 12.

Using these configurations, stimulation to achieve continence can be either unconditional or conditional. Unconditional stimulation is applied continuously, except when stopped by a manual signal. Conditional stimulation occurs in discrete intervals triggered by a manual or automatic (e.g. neural recoding) signal.

For example, as previously described, one form of an automatic control signal source 12 can comprise one or more electrodes 18 to 24 in the array 16 that are positioned to sense electroneurogram (ENG) activity in the whole pudendal nerve, or in individual efferent external anal sphincter branch (AMB) and/or efferent urethral sphincter branch (UMB). The recorded activity is processed by the pulse generator 14 to detect the onset of rectal contractions.

When the onset is detected by the pulse generator 14, a demand input is automatically transmitted. The pulse generator 14, in turn, automatically generates the desired waveforms to stimulate the afferent component and/or the efferent component, to thereby arrest the contractions and/or affect voluntary anal sphincter function, and thereby maintain fecal continence.

One form of a manual control signal source 12 can comprise the external controller 28 that the user manipulates. The external controller can take the form of a remote control switching device or magnetic reed switch. The manual controller 28 can be used in the place of or in combination with the ENG sensing electrodes or other form of automatic signal source 12.

For example, using the manual controller 28, the user can generate a fecal continence demand input, independent or in the absence of any automatic fecal continence demand input. In response, the pulse generator 14 applies electrical waveforms to the electrode or electrodes 18 to 24 in the array 16 that are positioned to stimulate the selected afferent component and/or the selected efferent component of the pudendal nerve trunk (PNT). Using the manual controller 28, the user can also terminate a fecal continence demand input. As a result, the user is able to "turn on" or "turn off" fecal continence control, depending, e.g., upon the time of day or food consumption. Using a manual controller 28, the user can also enable or disable an automatic fecal continence demand input source.

As another example, using the manual controller 28, the user can initiate a defecation demand input on their own volition. In response, the pulse generator 14 applies electrical waveforms to the electrode or electrodes 18 to 24 in the array 16 that are positioned to stimulate the selected afferent component and/or the selected efferent component of the pudendal nerve trunk (PNT). As a result, the user is able to defecate on demand.

In an alternative embodiment, the system 10 can be configured and operated to control peristalsis. In this arrangement, the system 10 include at least one electrode 18 sized and configured to be located on, in, or near a targeted component of the pudendal nerve away from a sacral root. The pulse generator 14 is coupled to the electrode 18 to apply an electrical signal to stimulate selectively a targeted afferent component of the pudendal nerve identified by a clinician to control peristalsis. The electrode 18 can comprise a single electrode or the multiple electrode array of the type shown in FIGS. 3 and 4. The electrode can be located on, in, or near an afferent branch of the pudendal nerve. Alternatively, the electrode can be located on, in, or near the pudendal nerve trunk. In this arrangement, the pulse generator 14 serves to stimulate selectively the identified afferent component in the pudendal nerve trunk. As with other lower bowel control functions, the pulse generator 14 can operate to apply the electrical signal in response to a volitional act of an individual. According to the pre-programmed rules expressed by the code embedded in the microprocessor 30, the pulse generator 14 directs prescribed stimulation waveforms through the leads 26 to those electrode or electrodes 18 to 24 in the array 16 that stimulate the targeted fascicle associated with the desired peristalsis control response. As also previously explained, the system 10 can include at least one recording electrode located in, on, or near the pudendal nerve or a branch of the pudendal nerve to sense electrical events indicative of peristalsis function. In this arrangement, the pulse generator 14 is coupled to the recording electrode and operates to apply the electrical signal in response to the sensed electrical events.

A response for controlling peristalsis (contraction of the colon) can be evoked by selective stimulation of one or more afferent components of the pudendal nerve. For peristalsis, selective stimulation of either or both afferent or efferent components can be undertaken to affect nerve activation to evoke the desire physiological responses.

As shown in FIG. 6, the manual controller 28 for lower bowel control can also be housed in a compact, lightweight, hand held housing 32, which desirable includes its own microprocessor 34 powered by a rechargeable, onboard battery (not shown). Additional features of the controller 28 when used for lower urinary tract control functions can also be used to achieve lower bowel control functions.

As with lower urinary tract control functions, the basic functional components for lower bowel control functions can be constructed and arranged in various ways. In one representative implementation, the electrode array 16, leads 26, and pulse generator 14 are all implanted. In this arrangement, the manual controller 28 comprises an external unit that is, e.g., magnetically coupled to the pulse generator 14, or coupled by a radio frequency link to the pulse generator 14 (e.g., in the manner as described in Peckham et al U.S. Pat. No. 5,167,229, which is incorporated herein by reference). Alternatively, a manual controller 28 can be coupled by percutaneous leads to the pulse generator 14.

V. Control of Sexual Functions

In another embodiment, the system 10 can be configured and operated to generate and distribute stimulus waveforms selectively to one or more components of the pudendal nerve trunk (PNT) to control sexual functions, such as—in males— erection, ejaculation, or orgasm, and—in females—vaginal lubrication or orgasm.

In one embodiment, the system 10 can be configured and operated to control erection in males and vaginal lubrication in females. In this arrangement, the system 10 include at least one electrode 18 sized and configured to be located on, in, or near a targeted component of the pudendal nerve away from a sacral root. The pulse generator 14 is coupled to the electrode 18 to apply an electrical signal to stimulate selectively the targeted component. The targeted component can comprise an afferent component of the pudendal nerve, which is identified by a clinician to dilate blood vessels and cause erection in a male, or lead to vaginal lubrication in a female, alone or in combination with other afferent components of the nervous system (e.g., ventral genital) and/or other efferent components of the nervous system.

In another embodiment, the system 10 can be configured and operated to control ejaculation in males. In this arrangement, the system 10 include at least one electrode 18 sized and configured to be located on, in, or near a targeted component of the pudendal nerve away from a sacral root. The pulse generator 14 is coupled to the electrode 18 to apply an electrical signal to stimulate selectively the targeted component. The targeted component can comprise an afferent component of the pudendal nerve, or an efferent component of the pudendal nerve, or both, which are identified by a clinician to contract pelvic muscles and cause ejaculation, alone or in combination with other afferent components of the nervous system (e.g., ventral genital) and/or other efferent components of the nervous system.

In another embodiment, the system 10 can be configured and operated to control orgasm in males or females. In this arrangement, the system 10 include at least one electrode 18 sized and configured to be located on, in, or near a targeted component of the pudendal nerve away from a sacral root. The pulse generator 14 is coupled to the electrode 18 to apply an electrical signal to stimulate selectively the targeted component. The targeted component can comprise one or more afferent components of the pudendal nerve which are identified by a clinician to evoke orgasm in an individual, alone or in combination with other afferent components of the nervous system (e.g., ventral genital) and other components of the nervous system.

In any of these embodiments, the electrode 18 can comprise a single electrode or the multiple electrode array 16 of the type shown in FIGS. 3 and 4. The single or multiple electrodes may be located on, in, or near the selected afferent branch of the pudendal nerve; or on, in, or near the selected efferent branch of the pudendal nerve; or both. Alternatively, a multiple electrode array 16 may be sized and configured to be located on, in, or near the pudendal nerve trunk, as FIG. 4 shows.

In this arrangement, the pulse generator 40 is coupled to the electrode array 16 to apply an electrical signal to stimulate selectively the selected afferent and/or efferent components of the pudendal nerve trunk.

As before explained in connection with the control of lower urinary tract functions, in controlling sexual functions, the pulse generator 14 can operate to apply the electrical signal in response to a volitional act of an individual. According to the pre-programmed rules expressed by the code embedded in the microprocessor 30, the pulse generator 14 directs prescribed stimulation waveforms through the leads 26 to those electrode or electrodes 18 to 24 in the array 16 that stimulate the targeted fascicle associated with the desired sexual response.

As shown in FIG. 6, the manual controller 28 for sexual control functions can also be housed in a compact, lightweight, hand held housing 32, which desirable includes its own microprocessor 34 powered by a rechargeable, onboard battery (not shown). Additional features of the controller 28 when used for lower urinary tract control functions can also be used to achieve sexual control functions.

As with lower urinary tract control functions, the basic functional components for sexual control functions can be constructed and arranged in various ways. In one representative implementation, the electrode array 16, leads 26, and pulse generator 14 are all implanted. In this arrangement, the manual controller 28 comprises an external unit that is, e.g., magnetically coupled to the pulse generator 14, or coupled by a radio frequency link to the pulse generator 14 (e.g., in the manner as described in Peckham et al U.S. Pat. No. 5,167,229, which is incorporated herein by reference). Alternatively, a manual controller 28 can be coupled by percutaneous leads to the pulse generator 14.

VI. Programming the Pulse Generator

In achieving any of the foregoing control functions, the pulse generator 14 can be linked to a remote computer for programming by a clinician. The programming allows a clinician to customize or "tune" the code residing in the microprocessor 30 of the pulse generator 14 according the specific needs of the user, the treatment goals of the clinician, and the particular anatomy of the pudendal nerve trunk associated with the electrode array 16.

A primary purpose of the programming is to adjust and store the location and operating parameters affecting the selection of electrodes 18, 20, 22, and 24 to perform the intended recording and/or targeted stimulation functions. During programming, logged data stored by the controller 28 can also be downloaded for assessment. The programming assesses which electrode or electrodes 18, 20, 22, and 24 are best positioned with respect to the various fascicles of the nerve branches in the pudendal nerve trunk (PNT), along with the operating parameters for each electrode 18, 20, 22, and 24, to affect the desired targeted degree of neural recording and/or neural stimulation for continence control or micturition control.

The programming maps the relative position of the implanted electrodes 18, 20, 22, and 24 with respect to the selected afferent and/or efferent components of the particular pudendal nerve trunk (PNT). With respect to each selected component, the programming refines the selected electrode or electrodes in terms of location and operating parameters, to obtain the desired, targeted stimulation result, as well as the desired, targeted neural recording, when desired. As before explained, whole nerve recording/stimulation can also be used.

The programming also determines the nature and character of electroneurogram (ENG) activity in pudendal nerve or the efferent external anal sphincter branch (AMB) and/or efferent urethral sphincter branch (UMB) that correspond with the onset of hyper-reflexive bladder contractions.

VII. Treatment Protocols and Choice

Another primary purpose of the programming is to install therapy or treatment protocols for the individual user. The treatment protocols establish the various physiological function demand inputs and the responding stimulation waveforms and their operating parameters and distribution. The treatment protocols also establish the automatic or manual nature of the various continence and micturition demand inputs.

When a programmable manual controller 28 of the type shown in FIG. 6 is used, the programming can also establish interaction between the manual controller 28 and the pulse generator 14. By programming the controller 28 and the pulse generator 14, the user can be provided with the ability to more closely control the operation of controller 28 and the pulse generator 14. By programming the controller 28 and the pulse generator 14, the user can be given the ability to select and modify operating parameters affecting his/her day-to-day life.

For example, the controller 28 can be programmed to list on the display 36 a menu 40 of choices (see FIG. 7). By operation of the keypad 38, the user can select Urinate. The selection generates the appropriate micturition demand input to the pulse generator 14 and results in bladder evacuation.

By operation of the keypad 38, the user can select Continence Auto Mode (On). The selection generates the appropriate input to the pulse generator 14 to enable the automatic generation of a continence demand input based upon neural sensing and results in automatic continuous continence maintenance.

By operation of the keypad 38, the user can select Continence Auto Mode (Off). The selection generates the appropriate input to the pulse generator 14 to disable the automatic generation of a continence demand input based upon neural sensing. By selecting Steady State Continence Control, the pulse generator 14 receives an appropriate continuous continence demand input. In response, the pulse generator 14 applies continuous stimulation. The result is manually controlled continuous continence maintenance.

With Continence Auto Mode (Off) selected, the user can also select Cyclical Continence Control. In response, the pulse generator 14 receives an appropriate cyclical continence demand input. The pulse generator 14 applies a cyclical stimulation waveform that, e.g., applies little or no stimulation at the outset of the stimulation period, but then increases the magnitude of the stimulation over time until a prescribed maximum degree of stimulation is achieved. The result is minimal continence maintenance at the outset (i.e., immediately after bladder evacuation), with an increasing degree of continence maintenance with the passage of time (as the bladder fills), until maximum degree of continence maintenance is achieved at or near the time when micturition is indicated. At this time, the user can select Urinate, and restart the cyclical stimulation waveform.

With Continence Auto Mode (Off) selected, the user can also select Continence Control (Off). In response, the pulse generator 14 receives no continence demand input. By subsequently selecting Steady State Continence Control or Cyclical Continence Control or Auto Continence Mode (On), the user can restart stimulation to affect continence.

As the following Table demonstrates, the system 10 may be configured and programmed to achieve diverse selective stimulation objectives involving nerve fascicles in the pudendal nerve trunk (PNT) or its branches, as well as other mixed or compound nerves within the body. Selectivity among nerve components can include the selection among the components within a compound nerve trunk, or among branches of a nerve trunk, or between afferent (sensory) or efferent (motor) nerve fibers with a given nerve structure, or selection with regard to size of nerve fibers, or with regard to direction of activation, or with regard to the functions of nerve activation (resulting in the generation of an action potential or impulse and its propagation along a nerve) or nerve inactivation or block (resulting in prevention of activation or propagation of an action potential or impulse).

Other nerve branches not specifically listed can also be recorded and/or stimulated to achieve desired therapeutic objectives.

TABLE

Representative Configuration and Operation of the System Involving the Pudendal Nerve Trunk or its Branches to Achieve Different Physiological Responses

| System | Control Function | Process | Selective Stimulation | |
|---|---|---|---|---|
| | | | Afferent Component | Efferent Component |
| Lower Urinary Tract | Continence | Relax/Inhibit Bladder | X (RI/RA) | |
| | | Contract Exterior Voluntary Urinary Sphincter | X (RA) | X (DA) |
| | | Contract Interior (Not Voluntary) Urinary Sphincter | X (RA) | |
| Lower Urinary Tract | Micturition | Contract Bladder | X (RA) | |
| | | Relax Exterior Voluntary Urinary Sphincter | X (RI) | X (DI) |
| | | Relax Interior (Not Voluntary) Urinary Sphincter | X (RI) | |
| Lower Bowel | Continence | Relax/Inhibit Rectum | X (RI/RA) | |
| | | Contract Exterior Voluntary Anal Sphincter | X (RA) | X (DA) |
| | | Contract Interior (Not Voluntary) Anal Sphincter | X (RA) | |
| Lower Bowel | Defecation | Contract Rectum | X (RA) | |
| | | Relax Exterior Voluntary Anal Sphincter | X (RI) | X (DI) |
| | | Relax Interior (Not Voluntary) Anal Sphincter | X (RI) | |
| Lower Bowel | Peristalsis | Contract Colon | X (RA) | X (DA) |
| Sexual | Erection | Dilate Blood Vessels | X (RA) | |
| Sexual | Vaginal Lubrication | Cause Lubrication | X (RA) | |
| Sexual | Ejaculation | Contract Pelvic Muscles | X (RA) | X (DA) |
| Sexual | Orgasm | Central Nervous System | X (RA) | |

Notes:
RA identifies reflex activation by stimulation of pudendal sensory nerve component(s), whereby control is achieved by activation of neural circuits in the central nervous system.
RI identifies reflex inhibition by stimulation of pudendal sensory nerve component (s), whereby control is achieved by inhibition of neural circuits in the central nervous system.
DA identifies direct activation by stimulation of pudendal motor nerve component(s), whereby control is achieved by activation of muscles (e.g., contraction of a sphincter).
DI identifies direct inactivation or block by stimulation of pudendal motor nerve component(s), whereby control is achieved by inactivation of muscles (e.g., relaxation of a sphincter).

Various features of the invention are set forth in the following claims.

We claim:

1. A method comprising
   identifying at least one desired physiologic function selected from the group consisting essentially of controlling a urinary tract function, controlling a bowel function, and controlling a sexual function,
   identifying at least two targeted afferent and/or efferent pudendal nerve components that, when selectively stimulated in combination, affect the desired physiologic function,
   placing an electrode configuration in a region of tissue away from a sacral root that includes the targeted afferent and/or efferent pudendal nerve components, and
   tuning the electrode configuration to achieve a combined selective electrical stimulation of the targeted afferent and/or efferent pudendal nerve components in the region to achieve the desired physiologic function.

2. A method according to claim 1
   wherein the targeted efferent pudendal nerve component comprises an efferent urethral nerve component.

3. A method according to claim 1
   wherein the targeted afferent pudendal nerve component comprises an afferent urethral nerve component.

4. A method according to claim 1
   wherein the targeted afferent pudendal nerve component comprises an afferent genital nerve component.

5. A method according to claim 1
   wherein the desired physiologic function comprises controlling urinary incontinence.

6. A method according to claim 1
   wherein the desired physiologic function comprises controlling micturition.

7. A method according to claim 1
   wherein the desired physiologic function comprises controlling ejaculation.

8. A method according to claim 1
   wherein the targeted afferent and/or efferent pudendal nerve components comprise at least one afferent pudendal nerve component and at least one efferent pudendal nerve component, and wherein the tuning achieves a combined electrical stimulation of the targeted afferent pudendal nerve component in the region in tandem with the targeted efferent pudendal nerve component in the region to achieve the desired physiologic function.

9. A method according to claim 8 wherein the targeted afferent and/or efferent pudendal nerve components comprise a urethral afferent nerve component and a urethral efferent nerve component, wherein the selective electrical stimulation of the targeted urethral efferent nerve component affects nerve inactivation and relaxation of a urinary sphincter, wherein the selective electrical stimulation of the targeted urethral afferent nerve component affects nerve activation and contraction of a bladder, and wherein the combined selective electrical stimulation achieves micturition.

10. A method according to claim 8 wherein the targeted afferent and/or efferent pudendal nerve components comprise a genital afferent nerve component and a urethral efferent nerve component, wherein the selective electrical stimulation of the targeted urethral efferent nerve component affects nerve activation and tightening of a urinary sphincter, wherein the selective electrical stimulation of the targeted genital afferent nerve component affects nerve activation and inhibition of bladder contractions, and wherein the combined selective electrical stimulation achieves urinary continence.

11. A method according to claim 1 wherein the tuning includes defining operating parameters for the electrode configuration.

12. A method according to claim 11 wherein the electrode configuration includes a single electrode.

13. A method according to claim 11 wherein the electrode configuration includes a multiple electrode array.

14. A method according to claim 1 wherein the region of tissue includes a pudendal nerve trunk.

* * * * *

UNITED STATES PATENT AND TRADEMARK OFFICE
CERTIFICATE OF CORRECTION

| | |
|---|---|
| PATENT NO. | : 7,623,925 B2 |
| APPLICATION NO. | : 11/141457 |
| DATED | : November 24, 2009 |
| INVENTOR(S) | : Grill et al. |

It is certified that error appears in the above-identified patent and that said Letters Patent is hereby corrected as shown below:

Drawing Sheet, in Figure 5, add "12" pointing to the box in the upper right corner (see attached Figure 5).

In column 4, line 7, delete "may undertaken" and insert --may be undertaken--.

In column 4, line 20, delete "desire" and insert --desired--.

In column 4, line 46, delete "desire" and insert --desired--.

In column 4, line 52, delete "desire" and insert --desired--.

In column 9, line 56, delete "arrests" and insert --arrest--.

In column 10, line 25, delete "desire" and insert --desired--.

In column 11, line 4, delete "may undertaken" and insert --may be undertaken--.

In column 11, line 11, delete "without volitional" and insert --without a volitional--.

In column 12, lines 8-9, delete "desirable" and insert --desirably--.

In column 12, line 40, delete "include" and insert --includes--.

In column 12, line 59, delete "desire" and insert --desired--.

In column 15, line 53, delete "desire" and insert --desired--.

In column 15, line 56, delete "desirable" and insert --desirably--.

Signed and Sealed this
Twenty-second Day of March, 2011

David J. Kappos
*Director of the United States Patent and Trademark Office*

CERTIFICATE OF CORRECTION (continued)
U.S. Pat. No. 7,623,925 B2

In column 16, line 44, delete "include" and insert --includes--.

In column 17, line 13, delete "desirable" and insert --desirably--.

In column 17, line 36, delete "according the" and insert --according to the--.

In column 17, line 64, delete "in pudendal" and insert --in the pudendal--.